(12) United States Patent
Leeflang et al.

(10) Patent No.: US 7,951,119 B2
(45) Date of Patent: May 31, 2011

(54) SLITTABLE OR REMOVABLE VALVES AND APPARATUS AND METHODS FOR MAKING AND USING THEM

(75) Inventors: Stephen A. Leeflang, Sunnyvale, CA (US); Christine P. Ventura, San Jose, CA (US); Christian S. Eversull, Palo Alto, CA (US); Nicholas J. Mourlas, Mountain View, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/603,602

(22) Filed: Oct. 22, 2009

(65) Prior Publication Data

US 2010/0042049 A1 Feb. 18, 2010

Related U.S. Application Data

(62) Division of application No. 11/687,653, filed on Mar. 18, 2007, now Pat. No. 7,621,894.

(60) Provisional application No. 60/800,130, filed on May 11, 2006, provisional application No. 60/784,040, filed on Mar. 20, 2006.

(51) Int. Cl.
*A61M 39/04* (2006.01)

(52) U.S. Cl. .................... 604/167.06; 604/158

(58) Field of Classification Search ........... 604/167.01–167.06, 96.01, 256, 604/158
See application file for complete search history.

(56) References Cited

U.S. PATENT DOCUMENTS

| 4,430,081 A | 2/1984 | Timmermans |
| 4,960,412 A | 10/1990 | Fink |
| 5,125,904 A | 6/1992 | Lee |
| 5,312,355 A | 5/1994 | Lee |
| 5,441,504 A | 8/1995 | Pohndorf et al. |
| 5,476,475 A * | 12/1995 | Gadberry ............ 606/185 |
| 5,858,007 A * | 1/1999 | Fagan et al. ......... 604/256 |
| 6,544,247 B1 | 4/2003 | Gardeski et al. |
| 6,712,791 B2 | 3/2004 | Lui et al. |
| 6,808,509 B1 | 10/2004 | Davey |
| 6,966,896 B2 | 11/2005 | Kurth et al. |
| 2003/0050604 A1 | 3/2003 | Lui et al. |

FOREIGN PATENT DOCUMENTS

| EP | 0198962 A1 | 10/1986 |
| GB | 2284452 | 6/1995 |
| WO | 98/00195 A1 | 1/1998 |

OTHER PUBLICATIONS

Partial European International Search Report for PCT/US2007/064251, dated Dec. 21, 2007.

* cited by examiner

*Primary Examiner* — Nicholas D Lucchesi
*Assistant Examiner* — Laura A Bouchelle

(57) ABSTRACT

A system and/or apparatus for delivering a medical device into a body includes an elongate tubular member and a valve fitted within a proximal end thereof. The valve preferably includes a tubular body and a flap, wherein the tubular body is engaged within the proximal end of the tubular member and has an open end approximately aligned with a proximal termination of the proximal end of the tubular member. The flap of the valve preferably extends over a hole formed in an end wall of the tubular body opposite a side of the end wall that faces a passage of the tubular body, which passage extends between the open end and the end wall. The hole communicates with the passage and with the lumen of the tubular member, and the flap is movable away from the hole when the device is introduced through the passage and the hole.

15 Claims, 7 Drawing Sheets

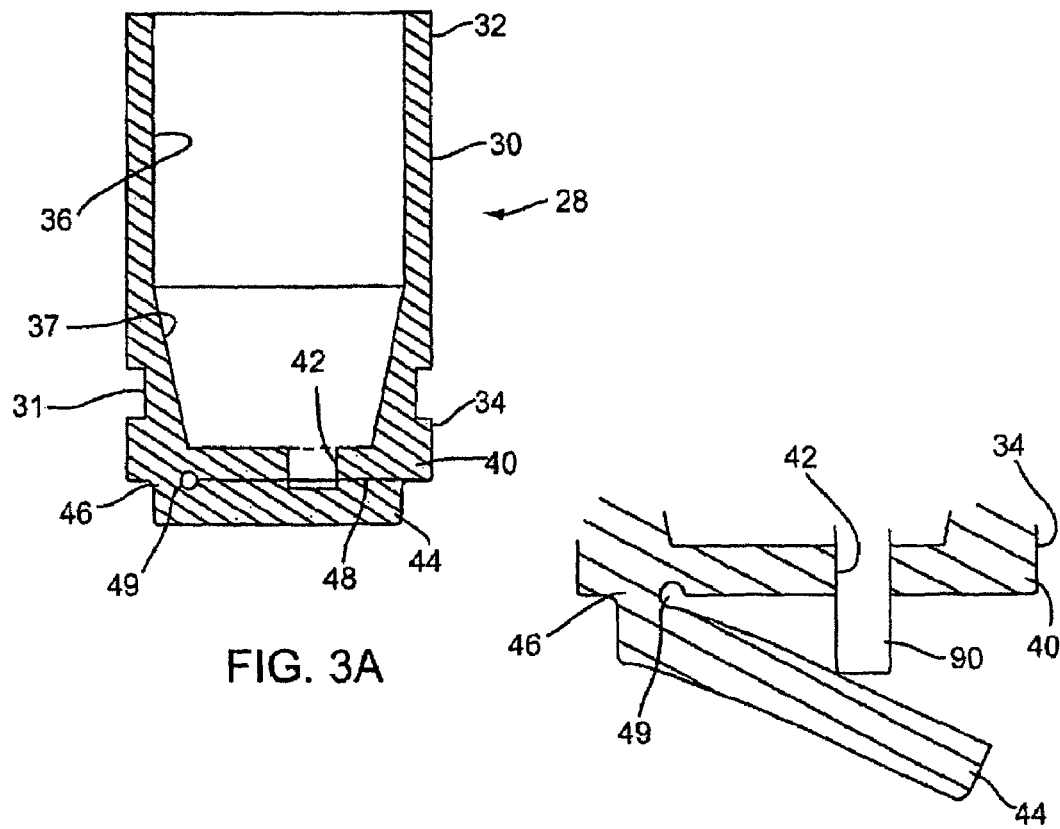
FIG. 3A
FIG. 3B
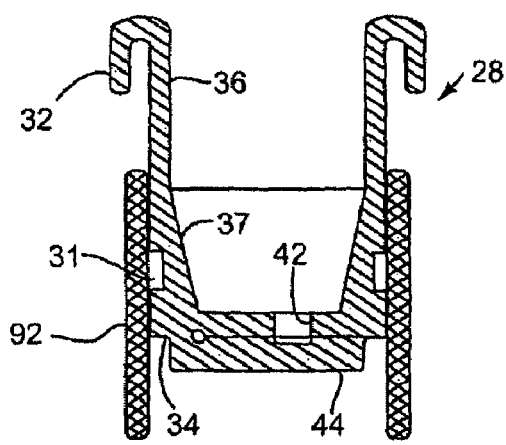
FIG. 4A
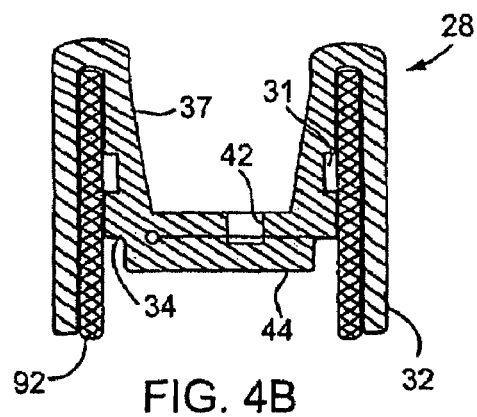
FIG. 4B

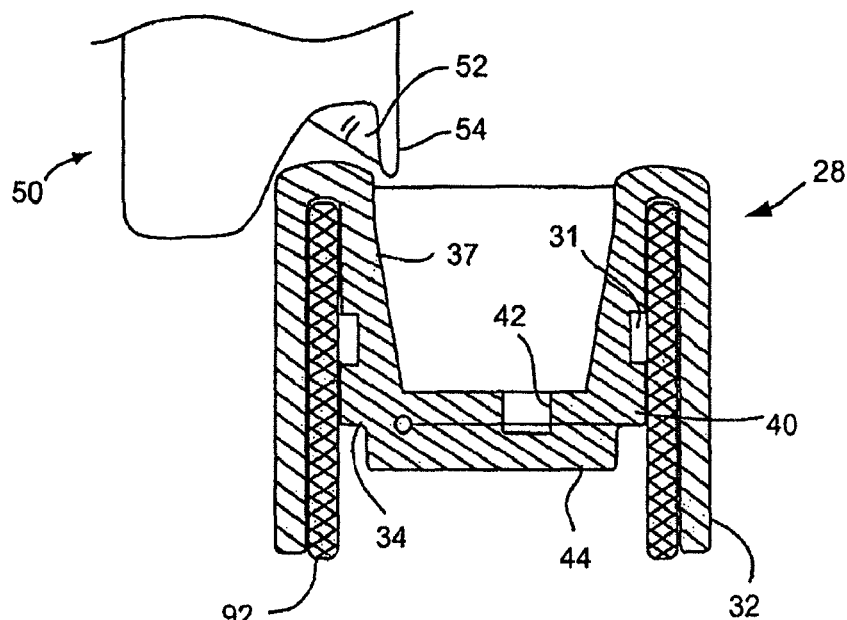
FIG. 5
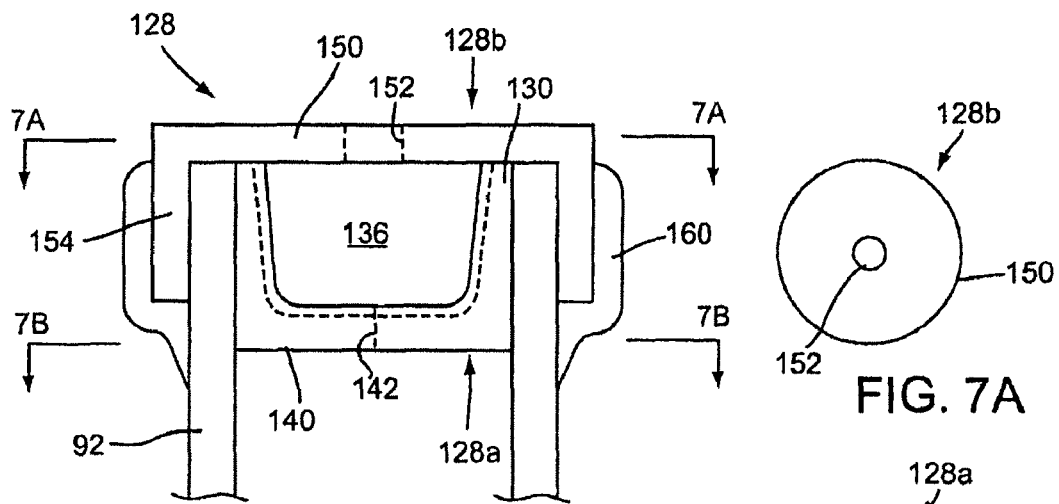
FIG. 6
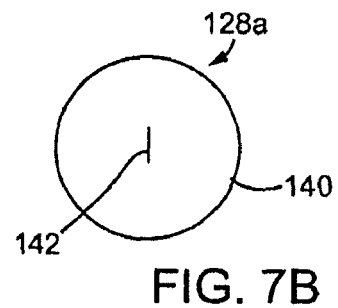
FIG. 7A
FIG. 7B

SLITTABLE OR REMOVABLE VALVES AND APPARATUS AND METHODS FOR MAKING AND USING THEM

The present application is a divisional of application Ser. No. 11/687,653, filed Mar. 18, 2007, which is now allowed and which claims the benefit of U.S. provisional application Ser. Nos. 60/784,040, filed Mar. 20, 2006, and 60/800,130, filed May 11, 2006, the entire disclosures of which are expressly incorporated by reference herein.

FIELD OF THE INVENTION

The present invention relates generally to apparatus and methods for delivering instruments and/or agents during a medical procedure, and, more particularly, to valves for guide sheaths, catheters, and other tubular devices for accessing body lumens and/or delivering instruments into body lumens of a patient and to methods for making and using them.

BACKGROUND

There are many medical procedures where a lead, catheter, electrode, and/or other medical device may be implanted into a patient's body cavity, recess, vessel, organ, and/or other lumen. In many of these procedures, a delivery sheath, guide catheter, or other tubular member may be used to facilitate delivering the medical device, with the tubular member removed after placement of the medical device. Additionally, it may be desirable to provide a seal or substantial seal between the delivery sheath, guide catheter, or other tubular member and the lead, catheter, electrode, and/or other medical device, e.g., for the purpose of hemostasis, infusion of therapeutic or diagnostic agents, and the like. However, the subsequent removal process can be difficult and time consuming.

For example, a delivery sheath used to deliver a cardiac lead may not be easily removed from around the lead without disturbing the placement of the lead, which must remain in the patient. Therefore, an apparatus that can facilitate the delivery of devices, provide a seal or substantial seal, and/or facilitate removal without substantially disturbing placement of the lead and/or other device may be desired.

SUMMARY

The present invention is directed generally to apparatus and methods for delivering instruments and/or agents during a medical procedure. More particularly, the present invention is related to valves for guide sheaths, catheters, and other tubular devices for accessing and/or delivering instruments into body lumens of a patient and to methods for making and using them. For example, slittable and/or removable valves may be provided, as well as methods for making and using them, and apparatus may be provided that include such valves.

In accordance with one embodiment, a valve is provided that includes a tubular body and a flap. The tubular body includes an open first end, a closed second end, and a passage extending between the first and second ends defining a central longitudinal axis, the second end comprising an end wall including a hole therein communicating with the passage. The flap is formed in the end wall over the hole and is movable away from the second end when an elongate device is introduced through the passage and the hole.

In one embodiment, the flap is integrally formed with the tubular body, e.g., as an injection molded assembly, and/or formed from elastomeric material.

In accordance with still another embodiment, a method is provided for making a valve that includes forming a tubular body comprising an open first end, a closed second end and a passage extending between the first and second ends defining a central longitudinal axis, the second end comprising an end wall including a recess communicating with the passage; and partially cutting the end wall transversely relative to the longitudinal axis to create a flap over the recess that is movable away from the second end such that the recess defines a hole through which an elongate device may be inserted.

In one embodiment, the tubular body is formed by injection molding, e.g., from an elastomeric material. Optionally, the method may include creating a channel through the end wall transversely relative to the longitudinal axis, and wherein the end wall is partially cut from an outer surface thereof to the channel such that the longitudinal channel at least partially defines a hinge allowing the flap to move away from the second end. In addition or alternatively, the method may include attaching the tubular body to a first end of a tubular device, e.g., a delivery sheath or a guide catheter.

In accordance with yet another embodiment, an apparatus is provided for delivering a medical device into a patient's body that includes an elongate tubular member including a proximal end, a distal end sized for introduction into a body lumen, and a lumen extending between the proximal and distal ends; and a valve attached to the proximal end. In one embodiment, the valve may include a tubular body including an open first end, a closed second end, and a passage extending between the first and second ends defining a central longitudinal axis. The second end may include an end wall including a hole therein communicating with the passage, and a flap formed in the end wall over the hole that is movable away from the second end when an elongate device is introduced through the passage and the hole.

In another embodiment, the valve may include a slit valve and a hole valve in series with one another. The slit valve may be configured to seal in a condition where no device is positioned through the valve, while the hole valve may be configured to seal in a condition where a device is placed through the valve into the lumen of the tubular member.

In accordance with still another embodiment, an apparatus is provided for introducing a device into a patient's body that includes an elongate tubular member including a proximal end, a distal end sized for introduction into a body lumen, and a lumen extending between the proximal and distal ends, the proximal end comprising a cavity therein; and a valve separate from the tubular member. The valve may be sized for insertion into the cavity, and may include a lumen disposed adjacent a side wall of the valve and a slit extending from the side wall to the lumen for receiving the valve around a portion of a medical device before introducing the portion of the medical device into the cavity.

In accordance with yet another embodiment, a method is provided for introducing a medical device into a patient's body. A distal end of a tubular member may be introduced into a body such that a proximal end of the tubular member remains outside the body. A valve may be attached around a portion of the medical device before introducing the portion of the medical device into the tubular member. The portion of the medical device may then be introduced into the a cavity in the proximal end of the tubular member with the valve thereon until the valve is received in the cavity, the valve providing a substantially fluid-tight seal between the proximal end of the tubular member and the medical device.

In accordance with still another embodiment, a system is provided for delivering a medical device into a patient's body that includes an elongate tubular member including a proximal end, a distal end, and a lumen extending between the proximal and distal ends for receiving a medical device therein; a valve attached to the proximal end in communication with the lumen; and a tool for slitting the valve and at least the proximal end of the tubular member.

In accordance with yet another embodiment, a method is provided for delivering a medical device into a patient's body. A distal end of a tubular member may be introduced into a body such that a proximal end of the tubular member remains outside the body. A medical device may be introduced through a valve attached to the proximal end and into the tubular member; and the valve and at least the proximal end of the tubular member may be slit to facilitate removal of the tubular member from around the medical device.

For example, the valve and the proximal end of the tubular member may be slit substantially simultaneously. In one embodiment, a slitter or other cutting tool may be used to slit the valve and the tubular member as the tubular member is removed from the patient's body from around the medical device. In an exemplary embodiment the tubular member may be a delivery sheath and the medical device may be a lead.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 3A is a cross-sectional view of a first embodiment of a valve that may be attached to the proximal end of the tubular device of FIGS. 1 and 2.

FIG. 3B is a cross-sectional detail of the valve of FIG. 3A with a device being inserted therethrough to open a flap of the valve.

FIGS. 4A and 4B are cross-sectional views showing a method for attaching the valve of FIGS. 3A and 3B to a tubular device, such as the proximal end of the tubular device of FIGS. 1 and 2.

FIG. 5 is a cross-sectional view of the assembled valve of FIGS. 4A and 4B being slit with a slitter.

FIG. 6 is a cross-sectional view of another embodiment of a valve attached to the proximal end of a tubular device.

FIGS. 7A and 7B are cross-sectional views of the valve of FIG. 6, taken along lines 7A-7A and 7B-7B, respectively.

DETAILED DESCRIPTION

Figure 1A:
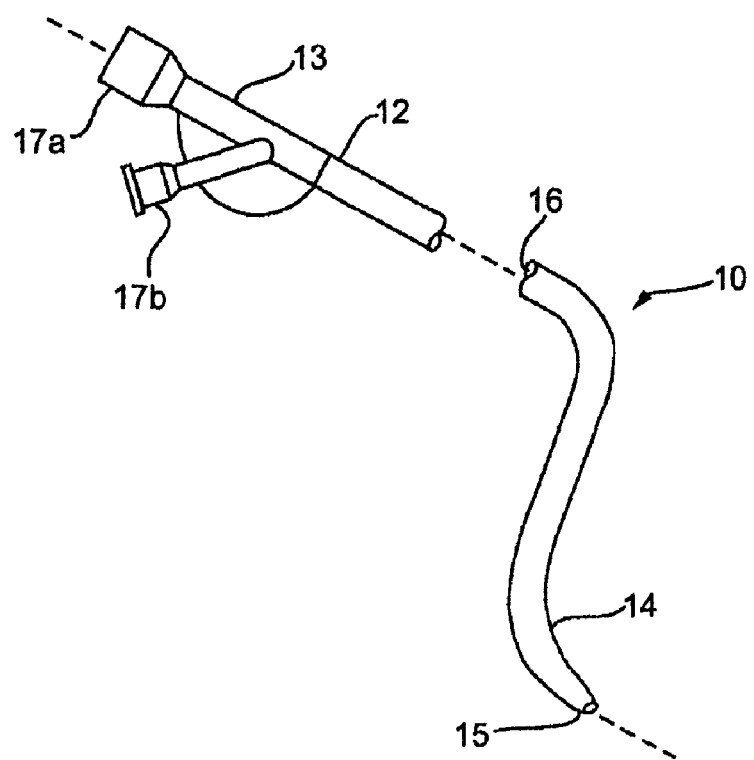
FIGS. 1A and 1B are perspective and longitudinal cross-sectional views, respectively, of an exemplary embodiment of a tubular device, including a lumen extending between proximal and distal ends thereof and a valve attached to a proximal end thereof and in communication with the lumen.
Figure 1B:
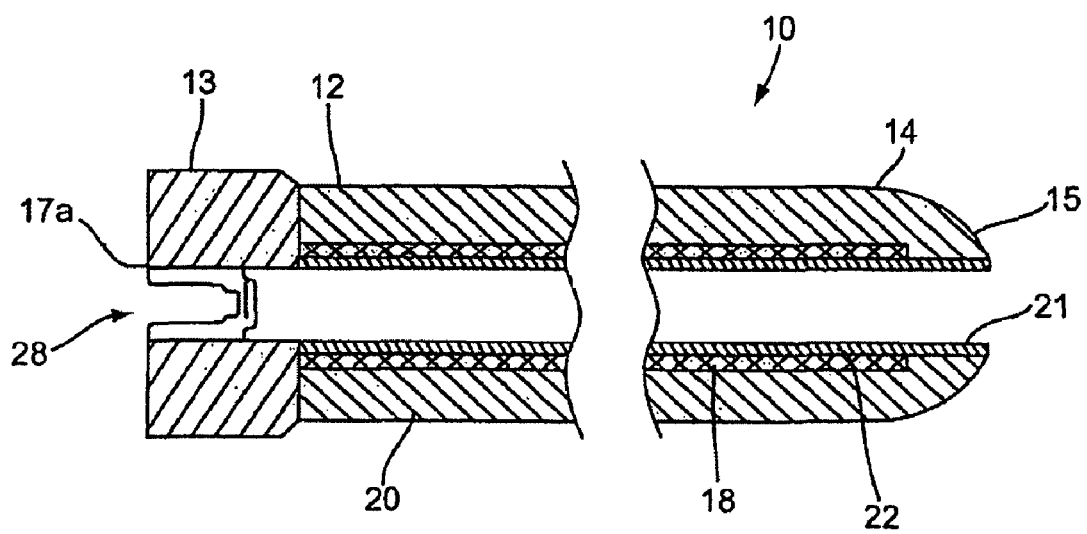

Turning to the drawings, FIGS. 1A and 1B show an apparatus 10 for accessing a body lumen (not shown) and/or for delivering one or more fluids, agents, and/or instruments (also not shown) within a body lumen. In exemplary embodiments, the apparatus 10 may be a delivery sheath, a guide catheter, a procedure catheter, an imaging device, or other tubular device that may be peeled apart, separated, or otherwise removed during use. The apparatus 10 may be sized for introduction into a body lumen, such as a vessel within a patient's vasculature, a passage within a patient's gastrointestinal tract, urogenital tract, reproductive tract, respiratory tract, lymphatic system, and the like.

Generally, the apparatus 10 is an elongate tubular member or device including a proximal end 12, a distal end 14 sized for introduction into a body lumen, a lumen 16 extending between the proximal and distal ends 12, 14, and a valve 28 for allowing one or more devices to be introduced into the lumen 16. Optionally, the apparatus 10 may include one or more additional lumens (not shown), which may be disposed concentrically around, side-by-side with, or otherwise adjacent the lumen 16. The lumen 16 may be sized for receiving a guide wire, procedure catheter, cardiac lead, needle, or other instrument (not shown), and/or for delivering fluids or other flowable agents or materials therethrough.

Optionally, the distal end 14 may include a tapered, rounded, or otherwise shaped distal tip 15, e.g., to provide a substantially atraumatic tip and/or to facilitate advancement or navigation through various anatomy. In addition or alternatively, the distal end 14 may include one or more therapeutic and/or diagnostic elements, e.g., one or more balloons, stents, sensors, electrodes, steering mechanisms, imaging devices, needles, and the like (not shown), depending upon the particular intended application for the apparatus 10.

Optionally, the proximal end 12 may include a handle 13 and/or one or more ports 17, e.g., main port 17a communicating with the lumen 16, and one or more side ports 17b (one shown) communicating with respective lumen(s) (not shown). In addition or alternatively, the handle 13 and/or proximal end 12 may include one or more connectors, such as luer lock connectors, electrical connectors, and the like, for connecting other devices (not shown) to the apparatus 10, such as syringes, displays, controllers, and the like (also not shown). In addition, the handle 13 may include one or more actuators, such as sliders, buttons, switches, and the like, e.g., for activating and/or manipulating components (also not shown) on the distal end 14 or otherwise operating the apparatus 10.

Optionally, the apparatus 10 may include one or more backbones or support members (not shown) that may extend at least partially between the proximal and distal ends 12, 14, e.g., as disclosed in co-pending application Ser. Nos. 10/423,321, filed Apr. 24, 2003, and 11/347,361, filed Feb. 3, 2006, the entire disclosures of which are expressly incorporated by reference herein.

Optionally, as shown in FIG. 1B, the apparatus 10 may be constructed from one or more layers, e.g., a reinforcing layer 18, an outer layer 20, and an inner layer 22 surrounding the lumen 16. The inner layer 22 may include a relatively thin film, sheet, or other material including an inner surface 21. The inner liner may be formed of a variety of materials to impart structural characteristics or for material properties.

For example, a fluoro-polymer liner may be added to impart lubricity. Alternatively, a coated liner may be added for properties of lubricity, anti-thrombogenicity, hydrophilic characteristic, and the like, as disclosed in co-pending application Ser. Nos. 11/340,904, filed Jan. 26, 2006, and 11/670,958, filed Feb. 2, 2007, the entire disclosures of which are expressly incorporated by reference herein.

The layers of the apparatus 10 may be attached to one another, e.g., by laminating, adhering, adhesive bonding, ultrasonic welding, reflowing or other heating, and the like. The construction of the apparatus 10 may be substantially uniform or may vary between the proximal and distal ends 12, 14 e.g., by varying the reinforcing layer 18, outer layer 20, and/or inner layer 22 along the length of the apparatus 10. Optionally, the outer layer 20, reinforcing layer 18, and/or inner layer 22 may include one or more sublayers (not shown), which may vary in construction in various portions of the apparatus 10.

In one exemplary embodiment, the proximal end 12 may be substantially rigid or semi-rigid, e.g., providing sufficient column strength to allow the apparatus 10 to be pushed from the proximal end 12, while the distal end 14 may be substantially flexible or semi-rigid. Thus, the distal end 14 of the apparatus 10 may be advanced or otherwise manipulated within a patient's body from the proximal end 12 without substantial risk of buckling and/or kinking. Optionally, the outer layer 20 at or adjacent the distal end 14 may be substantially flexible or semi-rigid and/or the reinforcing layer 18 may be terminated, e.g., to allow the distal end 14 to bend easily or otherwise be advanced through tortuous anatomy and/or provide a substantially atraumatic distal tip 15. For example, as shown in FIG. 1B, the reinforcing layer 22 may terminate within the distal end 14 proximal to the distal tip 15, e.g., to provide a relatively soft, flexible, and/or atraumatic distal tip 15.

In exemplary embodiments, the reinforcing layer 18 may include one or more round or flat wires, filaments, strands, braids, and the like. The material of the reinforcing layer 17 may be formed from metal, such as stainless steel, plastic, woven fibers, such as glass, Kevlar, and the like, or composite materials. Materials that may be used in the outer layer 20 may include one or more of PEBAX, urethane, FEP, PFA, polyethylene ("PE"), polyamide (Nylon), silicone, polypropylene, polysulfone, polyvinylchloride (PVC), polystyrene, polycarbonate, polymethylmethacrylate, fluoro-polymer, polyester, nylon, and the like. The inner layer 22 may include polyurethane, e.g., having a thickness between about 0.0001-0.01 inch (0.0025-0.25 mm), or other suitable polymers such as polyolefin, PEBAX, nylon, silicone, polypropylene, and polyethylene. Materials may be primarily selected for optimal mechanical, bonding, and/or other properties and subsequently imparted with desired surface properties, for example lubricity, by coating.

In exemplary embodiments, the apparatus 10 may have an outer diameter between about half and twenty millimeters (0.5-20 mm) or between about one and five millimeters (1-5 mm), and a length between about five and one hundred fifty centimeters (5-150 cm). The inner layer 22 may have a wall thickness between about 0.0001-0.01 inch (0.0025-0.25 mm) and the outer layer 20 may have a wall thickness between about 0.0005-0.2 inch (0.0127-5.08 mm).

With additional reference to FIGS. 3A and 3B, the valve 28 may be a hemostatic or other valve within and/or attached to the proximal end 12 of the apparatus 10, e.g., within the handle 13. The valve 28 may accommodate receiving one or more devices, e.g., a catheter, lead, guidewire or other device represented by exemplary device 90, through the valve 28 and into the apparatus 10, while preventing substantial proximal flow of fluid out of the apparatus 10.

Turning to FIGS. 3A-3B, an exemplary embodiment of a valve 28 is shown that generally includes a tubular body 30 including an open proximal or first end 32, a closed distal or second end 34, and a passage 36 extending between the proximal and distal ends 32, 34. The valve 28 includes an end wall 40 substantially closing the second end 34, the end wall 40 including a hole 42 therein communicating with the passage 36 and a flap 44. The flap 44 may be formed in or attached to the end wall 40, e.g., by a hinged region 46, such that the flap 44 is movable away from the second end 34 when an elongate device 90 (e.g., a catheter, lead, guidewire, and the like) is inserted through the passage 36 and hole 42, e.g., to accommodate receiving the device 90 through the valve 28.

The flap 44 and/or hinged region 46 may be biased such that, when no device 90 is received through the hole 42, the flap 44 covers the hole 42 and prevents substantial fluid leakage proximally through the valve 28, i.e., from the second end 34 to the first end 32. Thus, when fluid pressure is higher outside the flap 44 than within the passage 36, the flap 44 may maintain a substantial seal against the end wall 40 and prevent substantial fluid flow through the hole 42. Optionally, the flap 44 may open freely when fluid pressure is higher within the passage 36 than outside the flap 44.

The hole 42 may be sized appropriately to allow a device 90 to pass freely through the hole 42 without substantial frictional resistance and/or to provide a seal around the device 90 to prevent substantial fluid leakage when the device 90 is passed through the hole 42. Optionally, the end wall 40 may be substantially flexible such that the hole 42 may be dilated when a device 90 is inserted into the hole 42, and resiliently return to its original size when the device 90 is removed. In addition, the hole 42 may be sized appropriately to prevent and/or minimize prolapse of the flap 44 with or without the presence of pressure. For example, the hole 42 may be substantially smaller than the flap 44 such that the free end of the flap 44 may not easily fold or otherwise enter the hole 42.

Optionally, the flap 44 may include one or more stiffeners, reinforcement, or other features (not shown) to support the flap 44, e.g., to prevent prolapse of a portion of the flap 44 into the hole 42. In addition or alternatively, the flap 44 may include a plug or extension (not shown) that may extend at least partially into the hole 42 when the flap 44 is closed to enhance a seal and/or reduce prolapse. For example, a tab (not shown) shaped similarly to but slightly smaller than the hole 42 may be provided, e.g., bonded, integrally molded, or otherwise attached, to an inner surface of the flap 44 such that tab may be slidably received in the hole 42 when the flap 44 is closed. When the flap 44 is pushed open when a device 90 is inserted through the hole 42, the tab may simply slide out of the hole 42 to accommodate the device 90.

Optionally, the tubular body 30 may include one or more additional features. For example, the passage 36 within the tubular body 30 may at least partially taper, e.g., to facilitate introduction of a device 90 therethrough and/or into the hole 42. As shown in FIG. 3A, the passage 36 includes a tapered region 37 adjacent the end wall 40, which may guide a device introduced into the passage 36 towards the hole 24. In addition or alternatively, one or more external features may be provided to facilitate and/or enhance attachment of the valve 28 to a tubular device, such as apparatus 10 of FIGS. 1A and 1B. For example, as shown in FIG. 3A, the tubular body 30 may include an annular groove 31 around an exterior of the tubular body 30, which may provide a well for glue or other bonding materials to promote attachment of the valve 28 to a tubular member, such as handle 13 of FIG. 2. Alternatively, one or more annular ridges, tabs, detents, pockets, recesses, and the like (not shown) may extend from or into an exterior of the tubular body 30 to engage with mating features in a tubular member.

The valve 28 may be formed from an elastomeric material, such as silicone, chronoprene, isoprene, santoprene, and the like. In one embodiment, the valve 28 may be integrally formed as a single piece, e.g., by injection molding, casting, and the like. For example, with continued reference to FIG. 3A, the tubular body 30, including the end wall 40 may be integrally formed, e.g., by injection molding. The hole 42 may be a recess formed on an interior of the end wall 40 during molding, i.e., communicating with the passage 36 but not extending entirely through the end wall 40. As shown, the hole 42 may be offset radially from the central longitudinal axis 38, e.g., away from the hinged region 46, which may facilitate operation of the flap 44, as described elsewhere herein. Optionally, the hole 42 may be offset radially towards the hinged region 46, which may reduce the risk of prolapse of the flap 44.

The flap 22 may be formed by creating a transverse slit 48 partially through the end wall 40. For example, the end wall 40 may be cut using a blade, wire, saw, or other mechanical cutter, using a heated wire or other element, using a laser, and the like. The end wall 40 may be partially cut substantially perpendicularly to the longitudinal axis 38, e.g., from an outer edge of the end wall 40 near the hole 42 across the central longitudinal axis 38 without extending the cut entirely to the opposite outer edge. Thus, the remaining uncut portion of the end wall 40 may define the hinged region 46. The slit 48 may intersect the recess formed in the end wall 40 to create the hole 42, which may result in a partial recess being provided in the flap 22 overlying the hole 42 when the flap 44 is closed.

Optionally, the valve 28 may be formed with a hinge stress relief channel 49 that at least partially defines the hinged region 46. For example, a relatively small transverse channel 49 may be formed when the tubular body 30 is molded, e.g., using a relatively small, round rod or tube extending across a mold cavity having the desired shape of the tubular body 30. Alternatively, the channel 49 may be formed after molding or otherwise forming the tubular body 30, e.g., by drilling, coring, inserting a needle, and the like, transversely through the end wall 40. The channel 49 may extend substantially perpendicular to but radially offset from the central longitudinal axis 38, e.g., away from the hole 42. The slit 48 may then be extended into one side of the end wall 40 opposite the channel 49 towards and into the channel 49, e.g., such that the channel 49 provides a rounded base to the slit 48. The channel 49 may provide strain relief as the flap 44 swings open, e.g., by providing a curved, rather than blunt transition surface, which may distribute stresses as the flap 44 bends, e.g., when a device 90 is received through the hole 42, as shown in FIG. 3B.

With further reference to FIG. 3A, the valve 28, hole 42, and flap 44 may be adapted to maximize sealing when no device is passed through the hole 42. Further, the valve 28, hole 42, and flap 44 may be adapted to minimize or prevent prolapse of the flap 44 through the hole 42 under pressure, as described elsewhere herein. For example, the hole 42 may be concentrically aligned with the central longitudinal axis 38 or radially offset from the central axis 38.

Additionally, the valve 28 and/or the tubular member to which it is attached (such as apparatus 10 of FIGS. 1A and 1B)) may include one or more features for preventing spray from the valve 28 in the event of fluid leakage under pressure. For example, a disc with a slit or hole (not shown) may be provided, that may be formed from an elastomeric foam or other compliant material. In addition or alternatively, an annular brush, a slit valve, and/or a hole valve (not shown) may be provided within the valve 28, e.g., at the first end 32. Such features as a porous foam or a brush with many filaments may allow a small amount of leakage, thereby reducing the likelihood of pressure buildup, which may otherwise cause fluid to spray or squirt from the valve 28.

Turning to FIGS. 4A and 4B, an exemplary embodiment of a method is shown for attaching the valve 28 to a device hub, represented by tubular member 92. The tubular member 92 may be the proximal end 12 of an apparatus 10, such as that shown in FIG. 1A and/or a handle 13, such as that shown in FIG. 2, as described elsewhere herein. As shown, the tubular body 30 may be slightly smaller than the tubular member 92 such that the second end 34 of the tubular body 30 may be inserted into the tubular member 92, as shown in FIG. 4A. For example, the tubular body 30 may have a diameter smaller than between about half and twenty millimeters (0.5-20 mm) or between about one and five millimeters (1-5 mm).

The tubular body 30 may be slid into the tubular member 92 and have an interference fit, i.e., may fit snugly within the tubular member 92. Alternatively, the tubular body 30 may be folded or otherwise compressed to facilitate insertion into the tubular member 92, and may be sufficiently resilient to expand and engage the tubular member 92 when released. In addition or alternatively, the tubular body 30 and tubular member 92 may include mating connectors, e.g., one or more tabs or detents and pockets, ridges and grooves, and the like (not shown) that may engage one another when the second end 34 is sufficiently received in the tubular member 92. For example, one or more tabs (not shown) having a sloped edge closest to the end of the tubular member 92 and a blunt edge away from the end of the tubular member 92 may allow the tubular body 30 to slide over the tab(s) but thereafter prevent the tubular body 30 from being removed.

In addition or alternatively, the tubular body 30 may be bonded, fused, or otherwise attached to the tubular member 92. For example, an adhesive may be provided between the tubular body 30 and the tubular member 92, e.g., within the groove 31.

Turning to FIG. 4B, the first end 32 of the tubular body 30 may then be rolled or folded over the tubular member 92. The material of the tubular body 30 may be sufficiently flexible to be expanded when folded over the tubular member 92 and frictionally engage an outer surface of the tubular member 92. Optionally, the tubular body 30 may be formed from a heat-shrinkable material, or a band or other constraint (not shown) may be placed around the first end 32 and the tubular member 92, e.g., to provide a mechanical attachment of the valve 28 to the tubular member 92. For example, a heat shrinkable seal (not shown) may attach the valve 28 to the tubular member 92, e.g., forming the first end 32 of the tubular body 30 from a heat shrinkable material, such as PET, polyolefin, PTFE, and/or other suitable material, and blowing hot air or otherwise applying heat to cause the first end 32 to shrink around and frictionally engage the tubular member 92.

In addition or alternatively, an adhesive or other bonding or fusing may be used to attach the first end 32 around the tubular member 92. Alternatively, the valve 28 may be insert molded within, over, or around the tubular member 92. In another alternative, rather than folding or rolling the first end 32 over the tubular device 92, the first end 32 may removed from the entire assembly, e.g., by cutting the portion of the tubular body 30 exposed beyond the tubular device 92 when the second end 34 is received therein.

As described elsewhere herein, the tubular member 92 may be a catheter, sheath, or other medical device (not shown).

The attached valve 28 may facilitate delivering one or more catheters, pacing leads, electrodes, or other similar devices through the tubular member 92. The valve 28 may provide a substantial fluid seal and/or prevent substantial backflow during delivery of fluids, contrast dyes, and/or other diagnostic and/or therapeutic agents. Furthermore, the valve 28 may provide for hemostasis when the tubular member 92 is inserted into a blood vessel or other body lumen of a patient (not shown), e.g., to prevent substantial proximal flow of blood or other body fluids out of the tubular member 92.

Turning to FIG. 5, the valve 28 may be slittable along with the tubular member 92, e.g., to facilitate removal from around a lead or other device (not shown) delivered via the tubular member 92. For example, the valve 28 may be constructed from one or more elastomeric materials, such as silicone, natural rubber, synthetics rubbers, injection moldable elastomers, chronoprene, isoprene, santoprene, and the like, which may be easily cut with a slitter 50 or other cutting tool. The radial and longitudinal thickness of the valve 28 may be selected to facilitate ease of slitting. In addition or alternatively, the material and/or methods for attaching the valve 28 to the tubular member 92, e.g., heat shrink, glue, and/or features (not shown) incorporated into the tubular body 30 and/or tubular member 92 may be selected to facilitate slitting. In addition or alternatively, the thickness and/or length of the end wall 40 may be selected to facilitate slitting. For example, the side wall and/or the end wall 40 of the tubular body 30 may have a thickness between about 0.025-6 millimeters, e.g., about 0.025 inch (0.635 mm).

Optionally, the hole 42 may be positioned closer to one side of the tubular member 92, e.g., to facilitate ease of slitting. For example, the slitter 50 may include a blade 52 in a pocket adjacent a finger 54. The distance of the hole 42 from the wall of the tubular member 92 may be similar to the width of the pocket such that the finger 54 is received at least partially into the hole 42 when the slitter 50 is being used to cut the tubular member 92, which may facilitate cutting through the end wall 40.

Figure 8A:
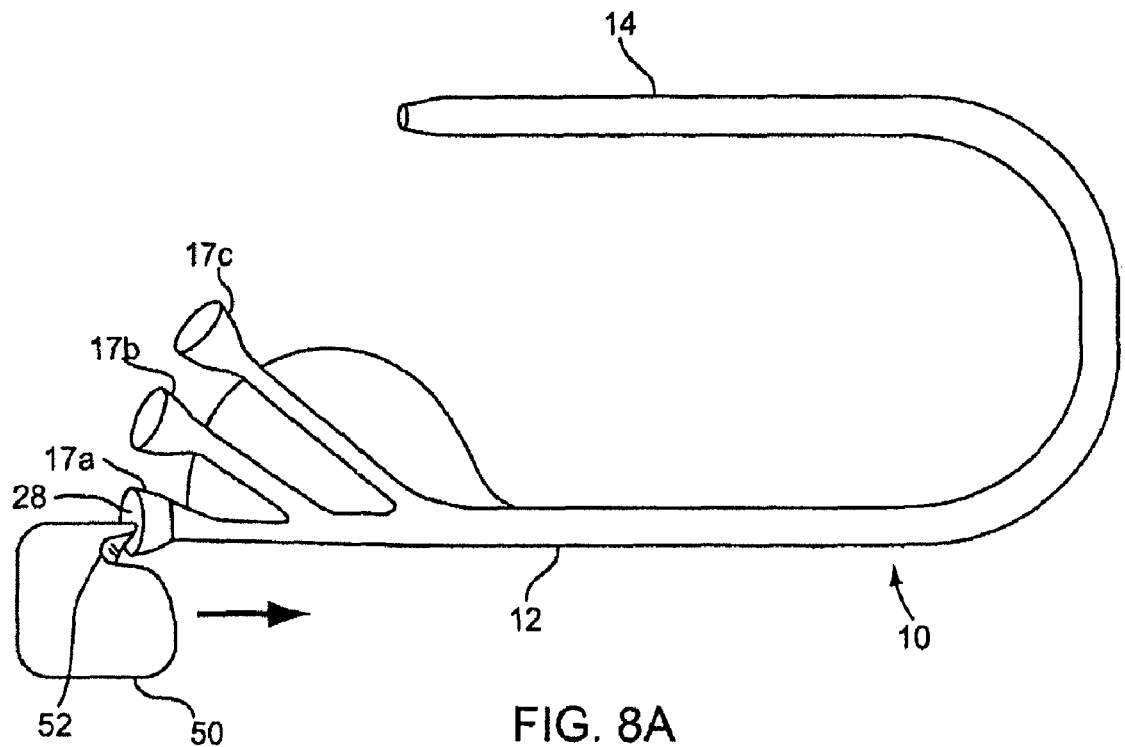
FIG. 8A is a side view of a tubular device including the valve of FIG. 6, being cut with a slitter.
Figure 8B:
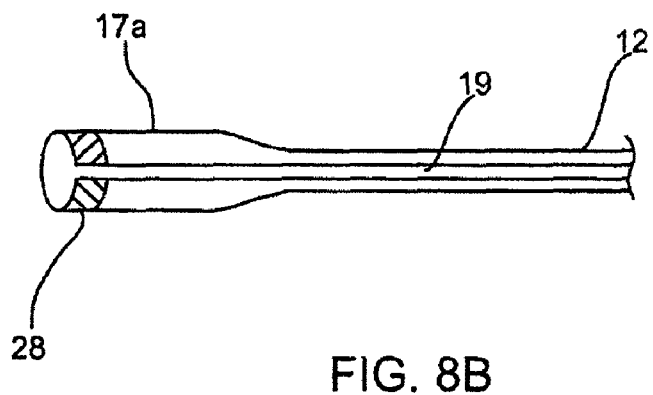
FIG. 8B is a detail of a tubular device that has been cut with a slitter.

With further reference to FIGS. 8A and 8B, an apparatus 10 (which may be any of the devices described elsewhere herein) is shown that includes a valve 28 (which may also be any of the embodiments described herein) within a port 17a on the proximal end 12 of the apparatus 10. After delivering a lead or other device (not shown) via the apparatus 10, the apparatus 10 may be removed from around the device by slitting, e.g., to facilitate sliding out the apparatus 10 around the delivered device. A slitter 50 may be inserted at the valve 28 such that the blade 52 cuts through the valve 28, the port 17a, and through the length of the apparatus 10, e.g., from the proximal end 12 to the distal end 14 as the apparatus 10 is pulled proximally from around the delivered device. In this manner, the apparatus 10 may be removed from a lead or other delivered device, while maintaining the delivered device within a patient's body.

Turning to FIG. 6, another embodiment of a hemostatic valve 128 is shown attached to a tubular member 92, which may any of the delivery apparatus described elsewhere herein. The tubular member 92 may be used to facilitate delivering one or more catheters, pacing leads, electrodes, and/or other devices, similar to embodiments described elsewhere herein. The valve 128 may provide a seal and/or prevent substantial backflow during delivery of fluids, contrast dyes, and/or other diagnostic and/or therapeutic agents. Furthermore, the valve 128 may provide for hemostasis when a device (not shown) is inserted into a blood vessel or other body lumen via the tubular member 92. In addition, the valve 128 may be slittable along with the tubular member 92 to facilitate removing the tubular member 92 from around the delivered device, e.g., similar to the other embodiments described herein.

With additional reference to FIGS. 7A and 7B, the valve 128 may be constructed such that the integrity of the seal is maintained whether or not a device (not shown) is positioned through the valve 128, e.g., by providing multiple different valve configurations in series with one another. For example, as shown in FIG. 6, the valve 128 may include two valve components, namely a slit valve 128a designed to seal in a condition where no device is positioned through the valve 128, and a hole valve 128b designed to seal in a condition where a device is placed through the valve 128, together facilitating a substantial seal in either condition. The components of the valve 128 may be constructed to facilitate ease of slitting. For example, the valve 128 may be constructed of one or more elastomeric materials, such as silicone, natural rubber, synthetics rubbers, injection moldable elastomers, chronoprene, isoprene, santoprene, and the like, similar to the other embodiments described herein.

With continuing reference to FIG. 6, the slit valve 128a may include a tubular body 130 sized to be received within the tubular member 92, similar to the previous embodiments. Unlike the previous embodiments, the tubular body 130 includes a slit 142 formed in an end wall 140 of the tubular body 130 and communicating with a passage 136 therein. The hole valve 128b may include an end wall 150 having a round hole 152 therethrough and a collar or cap 154 sized to be received over the tubular member 92. The two valve elements 128a, 128b may be attached to the tubular member 92, for example, using an interference fit, bonding with adhesive, RTV, solvent bonding, heat welding and the like. In addition or alternatively, a mechanical attachment may be provided by placing heat-shrinkable material 160 around the cap 154 of hole valve 128b and then heating the material 160, or by other suitable methods of attachment or bonding. The heat shrinkable material may include PET, polyolefin, PTFE, and/or other suitable materials. Alternatively, the valve and/or valves may be insert molded within and/or around the tubular member 92. In another alternative embodiment, the configuration of the valve components may be reversed, if desired, e.g., by switching the locations of the slit and hole valves.

Figure 2:
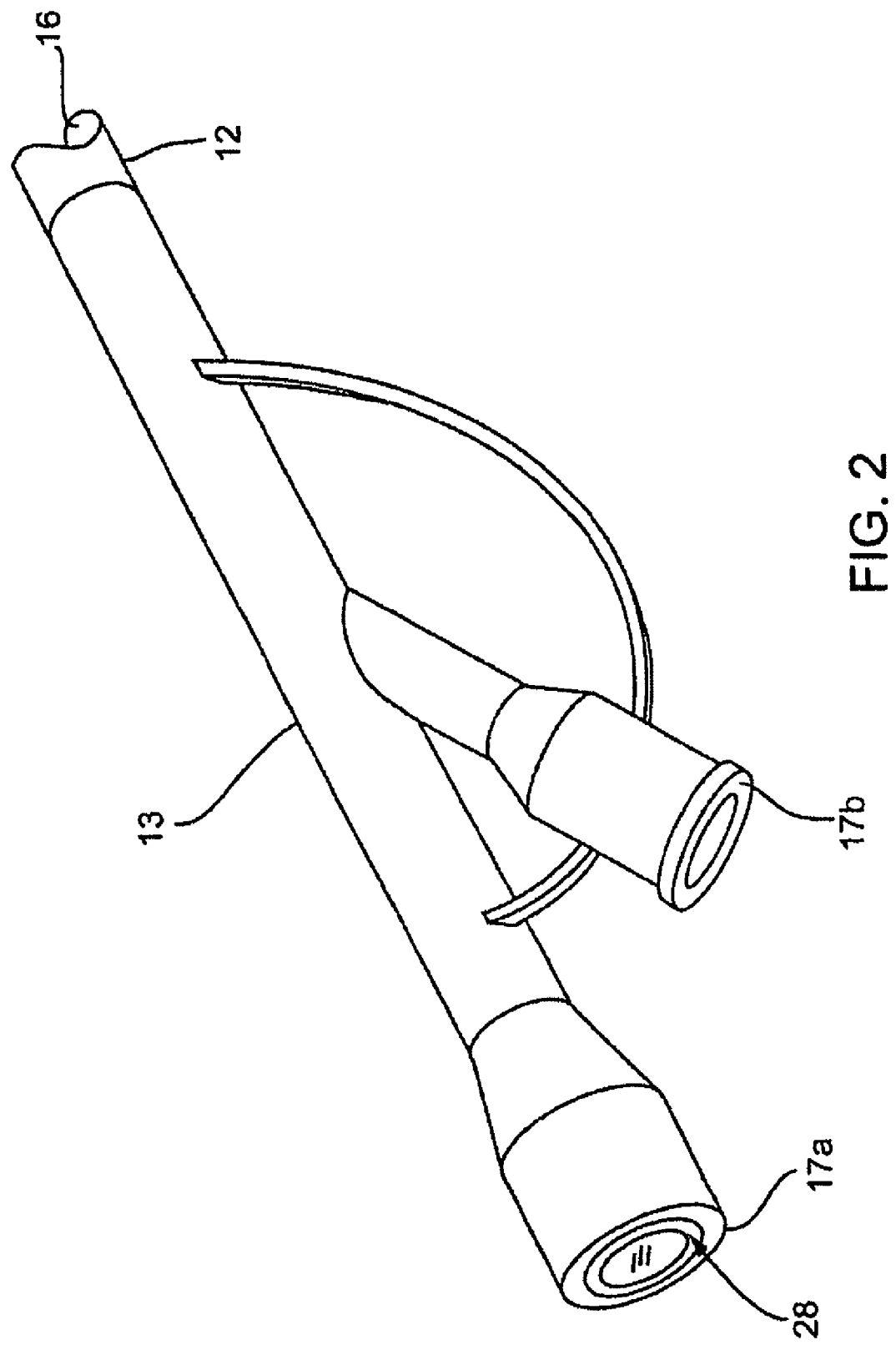
FIG. 2 is a perspective view of the proximal end of the tubular device of FIG. 1.
Figure 9A:
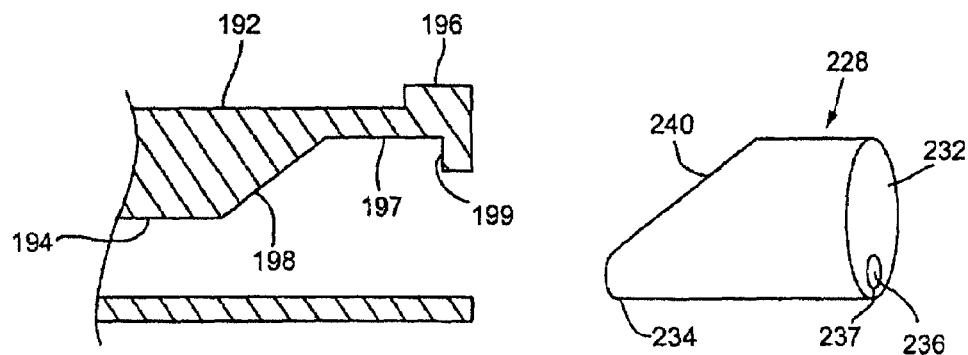
FIGS. 9A-9C are cross-sectional views of an exemplary embodiment of a removable valve being received within a proximal end of a tubular device.
Figure 9B:
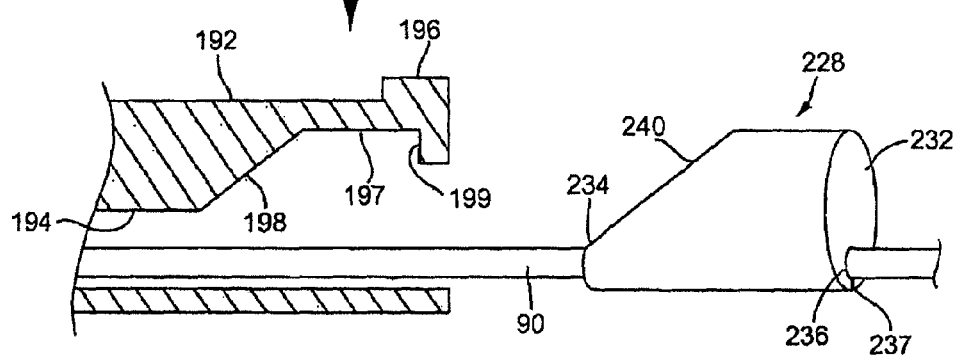
Figure 9C:
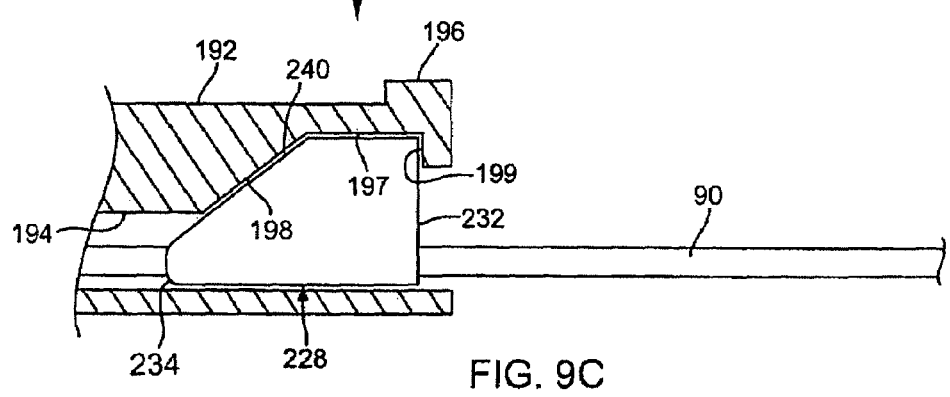

Turning to FIGS. 9A-9C, another embodiment of a valve 228 is shown that may be removably received within a tubular member 192, which may be the proximal end of an apparatus 10, as shown in FIG. 1A and/or a handle 13, as shown in FIG. 2. As shown, the tubular member 192 includes a hub 196 on one end communicating with a lumen 194. A cavity 197 is provided within the hub 196 that communicates with the lumen 194. As shown, the cavity 197 may be larger than the lumen 194, but may include a tapered transition region 198. In addition, the hub 196 includes a tab or ridge 199 that extends partially across the cavity 197.

Figures 10A, 10B:
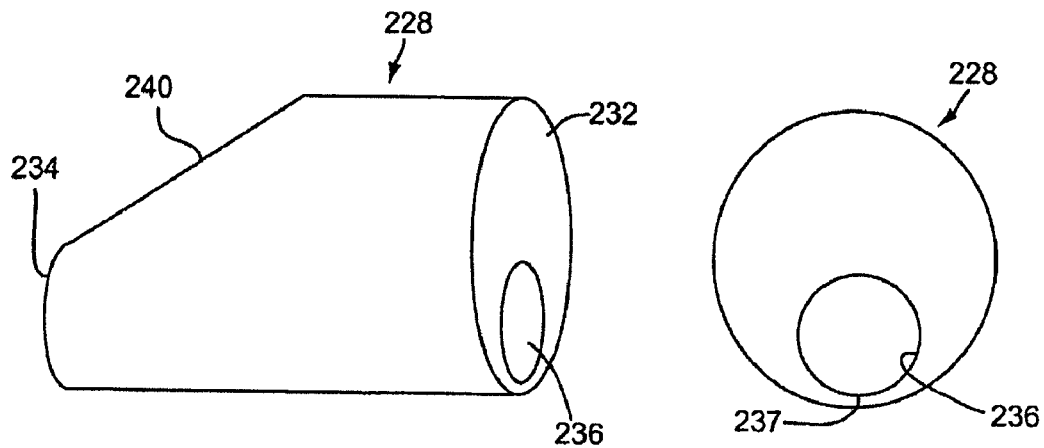
FIGS. 10A and 10B are side and end views, respectively, of the removable valve of FIGS. 9A-9C.
Figure 11A:
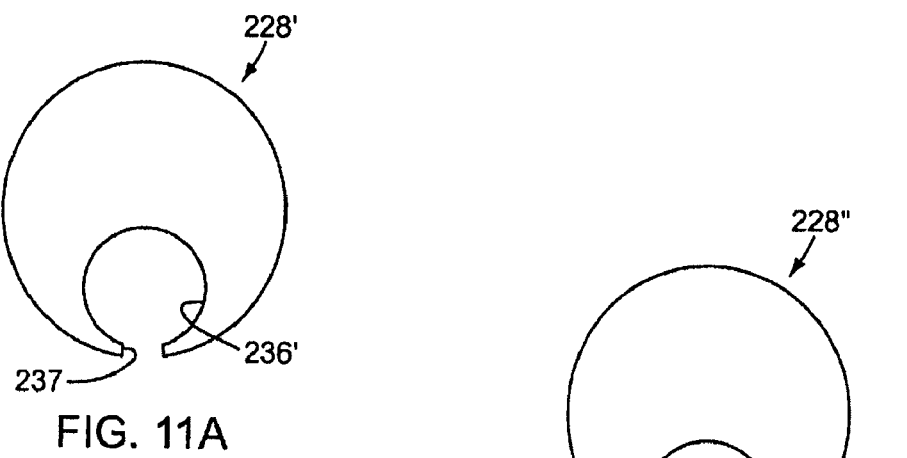
FIGS. 11A-11C are end views of alternative embodiments of a removable valve that may be received within the proximal end of the tubular device of FIGS. 9A and 9B.
Figure 11B:
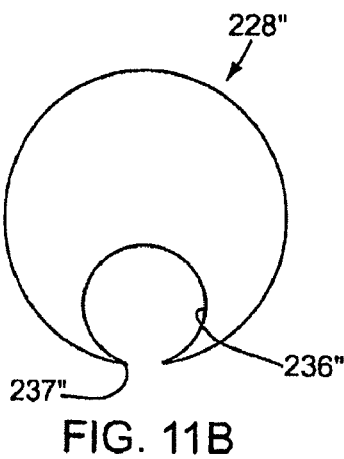
Figure 11C:
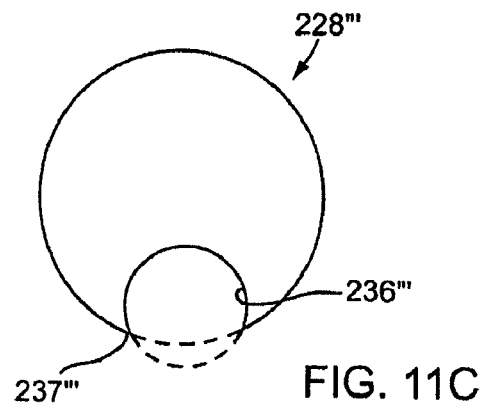

With additional reference to FIGS. 10A and 10B, the valve 228 includes first and second ends 232, 234, and a lumen 236 extending therebetween. As shown, the valve 228 may include a tapered region 240 or otherwise may be shaped similar to the cavity 197 within the hub 196. Optionally as shown, the lumen 236 may be disposed closer to one side wall of the valve 228, and a slit 237 may be formed in the relatively thin side wall that extends between the first and second ends 232, 234 and into the lumen 236. Alternatively, as shown in FIG. 11A, the valve 228' may include a lumen 236 that is formed as a cavity in the body of the valve 228' with a longitudinal gap defined by opposing edges 237.' In this alternative, the circumference of the lumen 236 is disposed entirely within the body of the valve 228' such that the opposing edges 237' have a desired thickness. In a further alternative, shown in FIG. 11B, the lumen 236" of the valve 228" is disposed immediately adjacent the side wall of such that the opposing edges 237." In another alternative, shown in FIG. 11C, the lumen 236'" of the valve 228'" only defines a portion of a circle, and the opposing edges 237'" are spaced further apart from one another than the other embodiments.

The valve 228 may be formed using any of the materials and methods described with reference to the other embodiments herein. The valve 228 may be similarly shaped with the cavity 197, but sized to slightly larger than the cavity 197 such that the valve 228 may fit tightly within the cavity 197.

Returning to FIGS. 9A-9C, during use the tubular member 192 and valve 228 may be provided initially separated from one another, as shown in FIG. 9A. Before or when a device 90 is inserted into the lumen 194 of the tubular member 192, the valve 228 may be attached to the device 90, as shown in FIG. 9B. For example, the valve 228 may positioned with the side with the slit 237 against the device 90. Force may then be applied to cause the slit 237 to open and allow the device 90 to pass through the slit 237 and into the lumen 236. The lumen 236 may have a size similar to the device 90 such that the valve 228 is slidable along the device 90. Alternatively, the lumen 236 may be slightly smaller than the device 90 such that the valve 228 grips around the device 90 to prevent substantial movement of the valve 228 along the device 90. Thus, for example, the valve 228 may received around a proximal end or other desired location on the device 90 and maintained there unless the friction between the valve 228 and the device 90 is overcome. A relatively smaller lumen 236 compared to the device 90 may also enhance a seal between the valve 228 and the device 90.

The device 90 may then be advanced into the tubular member 192 until the valve 228 enters the cavity 197 in the hub 196, as shown in FIG. 9C. The tapered region 240 of the valve 228 may facilitate introduction of the valve 228 into the cavity 197, e.g., past the tab or ridge 199. Optionally, the hub 196 may be sufficiently flexible to expand slightly as the valve 228 passes the tab or ridge 199, and return to its original size after the valve 228 is fully received within the cavity 197. Once the valve 228 is received within the cavity 197, the tab or ridge 199 may contact the first end 232, thereby preventing subsequent removal of the valve 228 from the hub 196. The device 90 may then be advanced further into and/or through the tubular member 192, if desired, e.g., by overcoming the frictional resistance between the valve 228 and device 90. The valve 228 may provide a substantial fluid-tight seal between the hub 196 and the device 90, thereby preventing body or other fluid from exiting the lumen 194 around the device 90.

Once the device 90 is positioned or otherwise delivered to a desired location within a patient's body, the hub 196 and valve 228, as well as the length of the tubular member 192 may be slit or otherwise cut, similar to the other embodiments described herein. Preassembling the valve 228 around the device 90 may facilitate introduction of the device 90 into the tubular member 192, while providing a hemostatic seal. For example, if the valve 228 were preinstalled in the hub 196 before introducing the device 90, enlarged regions or other features on a distal end (not shown) of the device 90 may not be easily inserted into the lumen 236 of the valve 228. Further, such enlarged regions or features may damage the valve 228 when passing therethrough, which may cause subsequent leakage between the valve 228 and the device 90. Alternatively, if the valve 228 is sufficiently resilient and/or the device 90 includes a substantially uniform distal end, the valve 228 may be inserted into the cavity 197 of the hub 196 before introducing the device 90 into the tubular member 192.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for introducing a medical device into a body lumen, comprising:
    an elongate tubular member including a proximal end, a distal end and a lumen, the distal end being sized for introduction into a body lumen, the lumen extending between the proximal end and the distal end and being sized to receive the medical device therein; and
    a valve being fitted within the proximal end of the tubular member, the valve comprising:
        a tubular body being engaged within the proximal end of the tubular member and including an open end, an end wall and a passage, the open end being approximately aligned with a proximal termination of the proximal end of the tubular member, the passage extending between the open end and the end wall and defining a central longitudinal axis of the tubular body, the end wall including a hole formed therein that communicates with the passage of the tubular body of the valve and with the lumen of the tubular member, the hole being radially offset from the central longitudinal axis of the tubular body, and
        a flap extending over the hole in the end wall, opposite a side of the end wall that faces the open end, the flap being movable away from the hole when the medical device is introduced through the passage and the hole.

2. The apparatus of claim 1, wherein the flap of the valve is integrally formed with the tubular body of the valve.

3. The apparatus of claim 1, wherein the valve comprises an injection molded assembly.

4. The apparatus of claim 1, wherein the tubular body of the valve and the flap of the valve comprise elastomeric material.

5. The apparatus of claim 1, wherein the valve further includes a channel extending transversely through the end wall, the channel at least partially defining a hinge between the flap and the tubular body of the valve.

6. The apparatus of claim 1, wherein the passage of the valve includes a tapered region adjacent the end wall of the valve, the tapered region configured to guide the device, when introduced therein toward the hole in the end wall.

7. The apparatus of claim 1, wherein the tubular body of the valve folds over the proximal termination of the proximal end of the tubular member.

8. The apparatus of claim 7, wherein the tubular body of the valve frictionally engages an outer surface of the proximal end of the elongate tubular member.

9. The apparatus of claim 1, wherein the tubular body of the valve includes a feature being formed on an external surface thereof to facilitate attachment of the fitted valve to an internal surface of the proximal end of the elongate tubular member.

10. The apparatus of claim 9, wherein the feature comprises a groove to hold adhesive.

11. The apparatus of claim 1, wherein the tubular body of the valve is engaged by an interference fit within the proximal end of the elongate tubular member.

12. An apparatus for introducing a medical device into a body lumen, comprising:
- an elongate tubular member including a proximal end, a distal end and a lumen, the distal end being sized for introduction into a body lumen, the lumen extending between the proximal end and the distal end and being sized to receive the medical device therein; and
- a valve being fitted within the proximal end of the tubular member, the valve comprising:
  - a tubular body being engaged within the proximal end of the tubular member and including an open end, an end wall and a passage, the open end being approximately aligned with a proximal termination of the proximal end of the tubular member, the passage extending between the open end and the end wall and defining a central longitudinal axis of the tubular body, the end wall including a hole formed therein that communicates with the passage of the tubular body of the valve and with the lumen of the tubular member,
  - a flap extending over the hole in the end wall, opposite a side of the end wall that faces the open end, the flap being movable away from the hole when the medical device is introduced through the passage and the hole; and
  - a channel extending transversely through the end wall, the channel at least partially defining a hinge between the flap and the tubular body of the valve.

13. An apparatus for introducing a medical device into a body lumen, comprising:
- an elongate tubular member including a proximal end, a distal end and a lumen, the distal end being sized for introduction into a body lumen, the lumen extending between the proximal end and the distal end and being sized to receive the medical device therein; and
- a valve being fitted within the proximal end of the tubular member, the valve comprising:
  - a tubular body being engaged within the proximal end of the tubular member and including an open end, an end wall and a passage, the open end being approximately aligned with a proximal termination of the proximal end of the tubular member, the passage extending between the open end and the end wall and defining a central longitudinal axis of the tubular body, the end wall including a hole formed therein that communicates with the passage of the tubular body of the valve and with the lumen of the tubular member, the tubular body of the valve folds over the proximal termination of the proximal end of the tubular member, and
  - a flap extending over the hole in the end wall, opposite a side of the end wall that faces the open end, the flap being movable away from the hole when the medical device is introduced through the passage and the hole.

14. An apparatus for introducing a medical device into a body lumen, comprising:
- an elongate tubular member including a proximal end, a distal end and a lumen, the distal end being sized for introduction into a body lumen, the lumen extending between the proximal end and the distal end and being sized to receive the medical device therein; and
- a valve being fitted within the proximal end of the tubular member, the valve comprising:
  - a tubular body being engaged within the proximal end of the tubular member and including an open end, an end wall and a passage, the open end being approximately aligned with a proximal termination of the proximal end of the tubular member, the passage extending between the open end and the end wall and defining a central longitudinal axis of the tubular body, the end wall including a hole formed therein that communicates with the passage of the tubular body of the valve and with the lumen of the tubular member, wherein the tubular body of the valve folds over the proximal termination of the proximal end of the tubular member and frictionally engages an outer surface of the proximal end of the tubular member, and
  - a flap extending over the hole in the end wall, opposite a side of the end wall that faces the open end, the flap being movable away from the hole when the medical device is introduced through the passage and the hole.

15. An apparatus for introducing a medical device into a body lumen, comprising:
- an elongate tubular member including a proximal end, a distal end and a lumen, the distal end being sized for introduction into a body lumen, the lumen extending between the proximal end and the distal end and being sized to receive the medical device therein; and
- a valve being fitted within the proximal end of the tubular member, the valve comprising:
  - a tubular body being engaged within the proximal end of the tubular member and including an open end, an end wall, a passage and a groove to hold adhesive formed on an external surface of the tubular body, the open end being approximately aligned with a proximal termination of the proximal end of the tubular member, the passage extending between the open end and the end wall and defining a central longitudinal axis of the tubular body, the end wall including a hole formed therein that communicates with the passage of the tubular body of the valve and with the lumen of the tubular member, the groove to facilitate attachment of the fitted valve to an internal surface of the proximal end of the elongate tubular member, and
  - a flap extending over the hole in the end wall, opposite a side of the end wall that faces the open end, the flap being movable away from the hole when the medical device is introduced through the passage and the hole.

* * * * *